US011234623B2

(12) United States Patent
Frick

(10) Patent No.: US 11,234,623 B2
(45) Date of Patent: Feb. 1, 2022

(54) NEEDLE ALIGNMENT FOR WEARABLE BIOSENSORS

(71) Applicant: DexCom, Inc., San Diego, CA (US)

(72) Inventor: Sean Frick, San Francisco, CA (US)

(73) Assignee: DexCom, Inc., San Diego, CA (US)

( * ) Notice: Subject to any disclaimer, the term of this patent is extended or adjusted under 35 U.S.C. 154(b) by 509 days.

(21) Appl. No.: 15/896,164

(22) Filed: Feb. 14, 2018

(65) Prior Publication Data

US 2018/0228416 A1 Aug. 16, 2018

Related U.S. Application Data

(60) Provisional application No. 62/458,934, filed on Feb. 14, 2017.

(51) Int. Cl.
*A61B 5/00* (2006.01)
*A61B 5/1486* (2006.01)
*A61B 5/145* (2006.01)

(52) U.S. Cl.
CPC ...... *A61B 5/14865* (2013.01); *A61B 5/14532* (2013.01); *A61B 5/688* (2013.01); *A61B 5/6848* (2013.01); *A61B 2560/063* (2013.01); *A61B 2562/12* (2013.01)

(58) Field of Classification Search
None
See application file for complete search history.

(56) References Cited

U.S. PATENT DOCUMENTS

| 5,568,806 A | * | 10/1996 | Cheney, II | A61B 5/14532 600/373 |
| 8,457,708 B2 | | 6/2013 | Brister et al. | |
| 2002/0016568 A1 | * | 2/2002 | Lebel | A61N 1/37211 604/131 |
| 2002/0119711 A1 | * | 8/2002 | VanAntwerp | A61B 5/14532 439/834 |

(Continued)

FOREIGN PATENT DOCUMENTS

WO 2007101223 5/2008

OTHER PUBLICATIONS

International Application No. PCT/US2018/018096, "International Search Report and Written Opinion", dated May 24, 2018, 9 pages.

(Continued)

*Primary Examiner* — Christian Jang
(74) *Attorney, Agent, or Firm* — Knobbe Martens Olson & Bear LLP

(57) ABSTRACT

Various examples are described for needle alignment for wearable biosensors. One example device includes a housing comprising an upper portion and a lower portion, the housing defining a cavity between the upper portion and the lower portion and configured to be worn on a wearer's skin, wherein: the upper portion defines a first opening extending through the upper portion to the cavity, and the lower portion defines a second opening extending through the lower portion to the cavity, the cavity establishing a substantially unobstructed pathway including the first opening and the second opening to enable an insertion needle to be inserted through the housing; and a needle guide extending into and along a portion of the pathway and aligned with a sensor wire to enable alignment between the insertion needle and the sensor wire.

20 Claims, 9 Drawing Sheets

(56) References Cited

U.S. PATENT DOCUMENTS

| | | | |
|---|---|---|---|
| 2004/0010207 A1* | 1/2004 | Flaherty | A61B 5/15113 |
| | | | 600/573 |
| 2006/0036145 A1* | 2/2006 | Brister | A61B 5/1495 |
| | | | 600/345 |
| 2006/0116607 A1* | 6/2006 | Nakamura | A61B 5/14532 |
| | | | 600/583 |
| 2011/0144597 A1 | 6/2011 | Woodruff et al. | |
| 2011/0213225 A1 | 9/2011 | Bernstein et al. | |
| 2011/0288574 A1* | 11/2011 | Curry | A61B 5/150427 |
| | | | 606/185 |

OTHER PUBLICATIONS

International Preliminary Reporton Patentability for Application No. PCT/US2018/018096 dated Aug. 29, 2019, 7 pages.

\* cited by examiner

CROSS-SECTION A

NEEDLE ALIGNMENT FOR WEARABLE BIOSENSORS

PRIOR RELATED APPLICATION

This application claims priority to U.S. Provisional Application No. 62/458,934, filed Feb. 14, 2017, entitled "Needle Alignment for Wearable Biosensors," which is hereby incorporated herein by reference in its entirety

BACKGROUND

Wearable biosensors may employ invasive components, such as sensor wires, that extend into the wearer's skin. Insertion of such sensor wires may be accomplished by first puncturing the wearer's skin with a needle and inserting the sensor wire into the puncture.

SUMMARY

Various examples are described for needle alignment for wearable biosensors. One example device includes a housing comprising an upper portion and a lower portion, the housing defining a cavity between the upper portion and the lower portion and configured to be worn on a wearer's skin, wherein: the upper portion defines a first opening extending through the upper portion to the cavity, and the lower portion defines a second opening extending through the lower portion to the cavity, the cavity establishing a substantially unobstructed pathway including the first opening and the second opening to enable an insertion needle to be inserted through the housing; and a needle guide extending into and along a portion of the pathway and aligned with a sensor wire to enable alignment between the insertion needle and the sensor wire.

One disclosed method includes forming an upper portion of a housing, the upper portion defining a first opening extending through the upper portion; forming a lower portion of the housing, the lower portion defining a second opening extending through the lower portion; physically coupling a support structure to at least one of the upper portion or the lower portion; physically coupling a sensor wire to the support structure and extending from the support structure; positioning a needle guide to extend into and along a portion of a pathway through the first and second openings, and aligned with the sensor wire; and physically coupling the upper portion to the lower portion to define a cavity between the upper portion and the lower portion and to position the sensor wire to extend through the second opening, the cavity extending from the first opening to the second opening and establishing a substantially unobstructed pathway including the first opening and the second opening to enable an insertion needle to be inserted through the housing.

Another disclosed method includes aligning a needle with a hole defined in an upper portion of a housing of a wearable medical device, the housing comprising an upper portion and a lower portion, the housing defining a cavity between the upper portion and the lower portion, wherein: the upper portion defines a first opening extending through the upper portion to the cavity; the lower portion defines a second opening extending through the lower portion to the cavity, the cavity extending from the first opening to the second opening and establishing a substantially unobstructed pathway including the first opening and the second opening, a support structure is disposed within the cavity and physically coupled to at least one of the upper portion or the lower portion, a sensor wire is physically coupled to the support structure and extending from the support structure into the pathway and through the second opening, and the needle has a cross-section corresponding to a perimeter of the first opening, aligning the needle with a needle guide extending into and along a portion of the pathway and aligned with the sensor wire; inserting the needle through the wearable medical device at an insertion angle; inserting the needle into a wearer's skin to create a puncture; inserting the sensor wire into the puncture; physically coupling the housing the wearer's skin; and withdrawing the needle from the wearer's skin and the housing.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
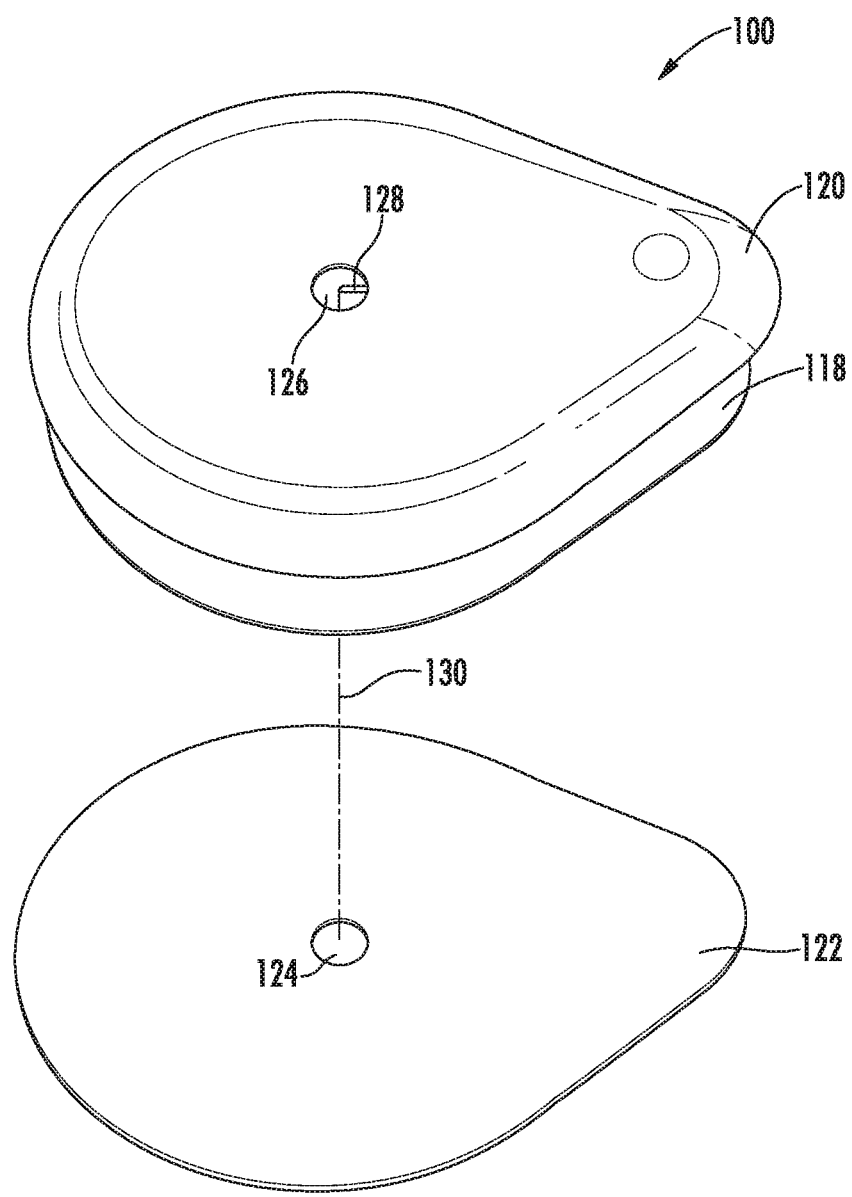
FIG. 1 shows an example housing having a needle alignment feature for a wearable biosensor.

Examples are described herein in the context of needle alignment for wearable biosensors. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In one illustrative example, a person obtains a new continuous glucose monitor ("CGM") that she can use to monitor her glucose levels. Based her glucose level at any given time, she can determine whether to administer a dose of insulin or eat some food. Her new CGM is a wearable device that she can adhere to her body, such as in the abdominal region or on her arm, and that includes a small sensor wire that she will insert into her skin when she applies the CGM. The sensor wire will then remain inserted into her skin for the lifetime of the CGM—such as for a couple of weeks—and provide sensor signals to the CGM, which can be interpreted as glucose levels and provided to a monitoring device, such as her smartphone or an insulin pump.

In this example, the sensor wire is substantially 5-10 millimeters ("mm") long and substantially 100 microns in diameter. With such dimensions, the sensor wire may be fragile and prone to bending or breaking. Because human skin is relatively resistant to puncturing, the sensor wire is likely to be damaged if she tries to simply press it into and through her skin Therefore, she uses an applicator to assist with inserting the sensor wire into her skin.

The applicator uses a needle that can be inserted into a hole in the upper side of the CGM. The hole runs through the entire height of the CGM to corresponding hole on the bottom side of the CGM at substantially the same location the sensor wire protrudes from the CGM, forming a pathway between the two holes that the needle can traverse. Thus, by inserting the needle through the upper hole and the pathway, it will exit through the lower hole and protrude from the underside of the CGM and can be used to puncture the wearer's skin. The sensor wire can then be inserted through the puncture.

However, the size of the sensor wire makes it likely that the wire may be damaged if it is struck by the needle, such as when the needle is inserted through the CGM. To help prevent damage to the sensor wire and to align the needle with the wire, a needle guide is provided within the pathway. For example, the hole on the upper surface of the CGM has a circular cross-section and a small tab or protrusion is positioned below the hole such that it extends from the perimeter of the hole towards the center of the hole. Since the needle is straight, the needle guide extends downward within the pathway along an axis running through the center of the hole, from top to bottom. Thus, in this example, the tab (or protrusion) extends from the perimeter of the hole to this axis. In addition, the tab is formed such that, when looking down through the hole, it extends above the sensor wire, thereby shielding the sensor wire from the needle when the needle is inserted into the hole and preventing the needle from rotating and striking the needle, and through the CGM to align the needle along a substantially common axis with the sensor wire to allow the needle to puncture the person's skin and the sensor wire to enter the person's skin through the puncture.

Because the tab extends into the insertion hole, the needle supplied with the CGM does not have an uninterrupted circular cross-section. Instead, the needle has a circular cross-section with a channel extending the length of the needle, which gives the needle a C-shaped cross-section. When inserted into the hole, the channel in the needle is aligned with the tab to allow the needle to pass through the hole and through the CGM.

After inserting the needle through the CGM, she uses the needle to puncture her skin as she presses the CGM against her skin, thereby also inserting the sensor wire through the puncture and into her skin. In addition, an adhesive on the underside of the CGM adheres to her skin to hold the CGM in place. Once the CGM is in place, she is then able to use the applicator to withdraw the needle from the CGM to leave the CGM and sensor wire adhered to her body.

This illustrative example is given to introduce the reader to the general subject matter discussed herein and the disclosure is not limited to this example. The following sections describe various additional non-limiting examples of needle alignment for wearable biosensors.

Referring now to FIG. 1, FIG. 1 shows an example housing 100 for a wearable biosensor. Some types of biosensors may obtain biometric information via a sensor wire that is inserted into the wearer's skin. However, as discussed above, because sensor wires for biometric sensors can have diameters less than 100 microns, they may not be strong enough to puncture a person's skin without bending or breaking. Thus, to insert the sensor wire, a needle may be used to first puncture the skin, after which the sensor wire can be inserted through the puncture. To facilitate the use of the needle, the example housing shown in FIG. 1 provides a cavity in which a sensor wire and associated electronics can be inserted as well as two holes 126 and 124 to accommodate a needle and defining upper and lower portions of a pathway through the housing 100 for the needle to traverse.

The housing 100 in this example includes two separate housing portions—upper portion 120 and lower portion 122—that together define an interior cavity into which sensor electronics and other components can be installed, though it should be appreciated that the housing 100 may comprise more than two portions, or may be formed as a single piece. The upper portion 120 of the housing 100 has an upper surface in which a hole 126 is defined. Similarly, the lower portion 122 has a lower surface in which a second hole 124 is defined. The two holes 124, 126 have circular cross-sections in this example such that the holes 124, 126 can receive a needle having a substantially circular cross-section, where the cross-sections are taken in parallel cross-sectional planes through the respective openings or needle. In other examples, however, the holes 124, 126 may have any suitable cross-section corresponding to a desired needle shape, may have different cross sections, or may have different sizes.

As can be seen in FIG. 1, a needle guide 128 is provided in the housing 100. In this example, the needle guide 128 is physically coupled to an inner surface of the upper portion 120 and extend downward from the upper portion 120. In addition, the needle guide 128 is positioned to extend from the perimeter of the hole 126 radially towards the hole's center. The needle guide 128 in this example is formed from the same material as the upper portion 120 of the housing 100 when the upper portion 120 is injection molded or cast. However, the needle guide 128 could be created by any suitable process, such as adhering or welding the needle guide 128 to the upper portion 120, the lower portion 122, or as a separate component within the interior cavity. The needle guide's presence can impede or prevent a needle having a circular cross-section, while allowing a needle having a complementary cross-section, such as a C-shaped cross-section, a half-moon or hemispherical cross-section, etc., to engage with the needle guide 128 and to traverse the pathway between the holes 124, 126.

Figure 2A:
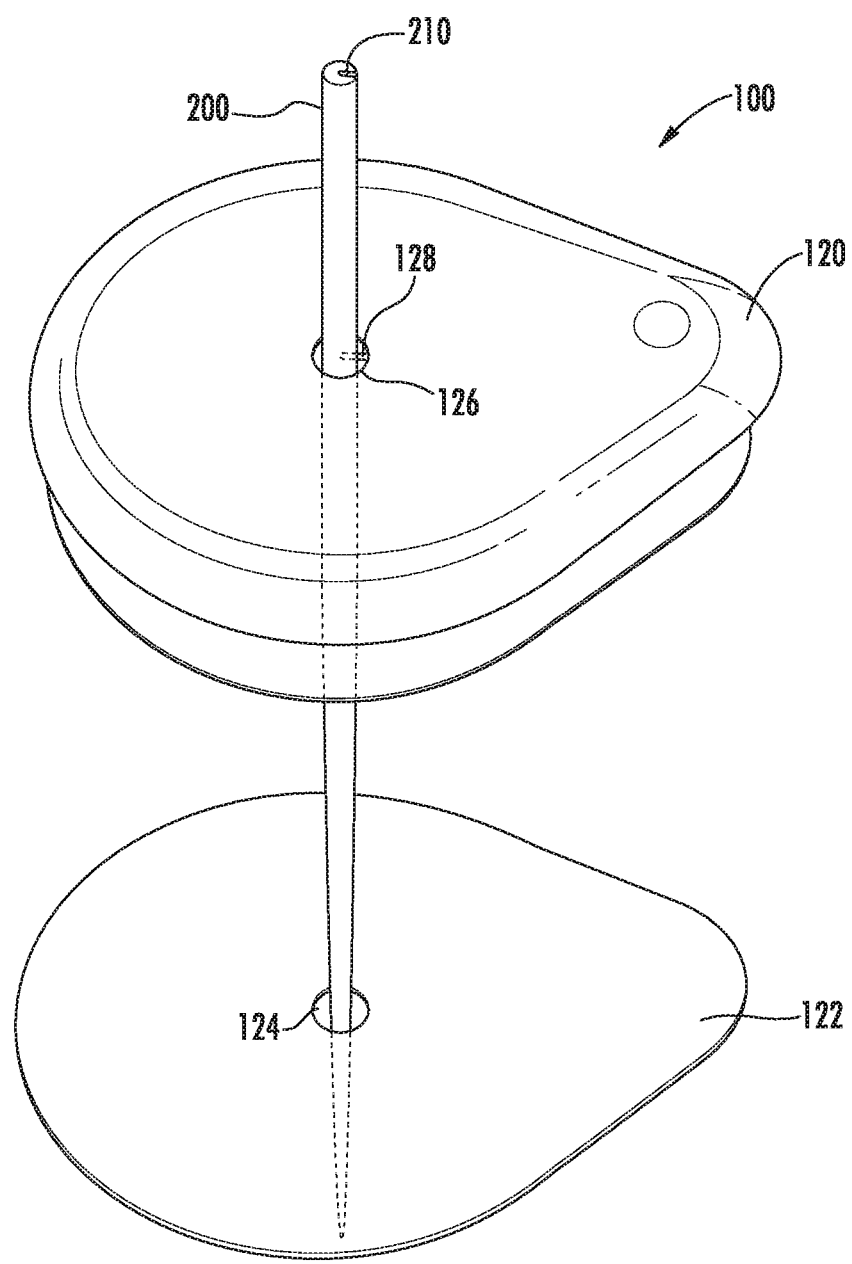
FIGS. 2A-2C show an example needle for use with a needle alignment feature for wearable biosensors.

FIG. 2A illustrates a needle 200 having a C-shaped cross-section inserted through the housing via the two holes 126, 124. As can be seen the needle 200 has a channel 210 running the length of the needle 200 that engages with the needle guide 128. In this example, because the needle 200 has engaged with the needle guide 128, it is guided along a specific path and at a particular orientation through the housing 100.

Figure 2B:
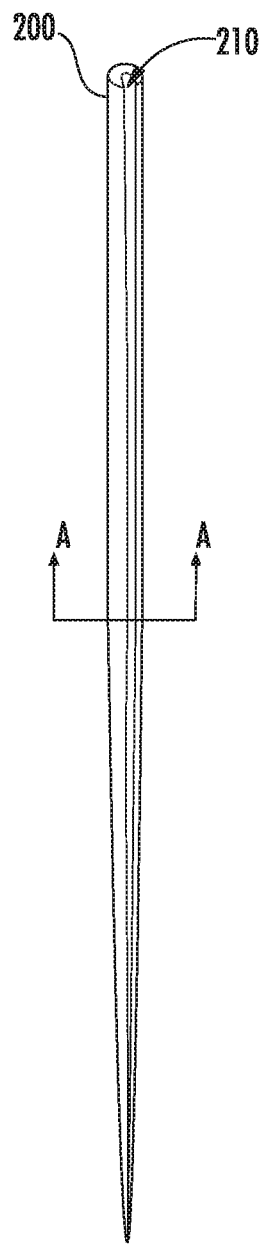
Figure 2C:
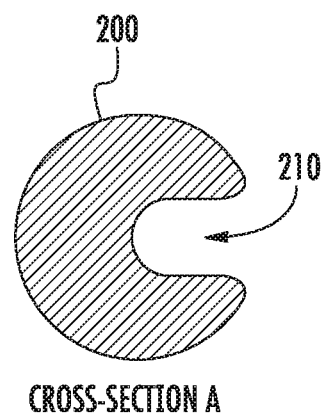

FIGS. 2B and 2C show the example needle 200 in isolation, while FIG. 2C shows a cross-section of the needle 200 to illustrate the C-shaped cross-section with the channel 210. It should be appreciated that while the example needle 200 shown in FIGS. 2A-2C has what is referred to as a "C-shaped" cross section, any suitable cross-section, including examples having curved, polygonal, etc. partial cross-sections, that also define one or more channel or channels to enable the needle to engage with a needle guide and traverse a common, or substantially common, axis as a sensor wire.

Referring again to FIG. 1, the hole 124 in the lower portion 122 of the housing 100 is positioned such that the center of the hole 126 in the upper portion 120 aligns along an axis with the center of the hole 124 in the lower portion 122. In this example, the axis 130 runs perpendicular to the upper surface of the upper portion 120 and to the plane of the lower surface 122. However, in some examples, the two holes 124, 126 may be offset such that the axis is angled with respect to the upper surface of the upper portion 120 and the plane the lower surface 122. In some examples, the angle may be anywhere from 0 to 60 degrees offset from an axis, e.g., axis 130, perpendicular to the upper surface of the upper portion 120 and the plane the lower surface 122. This angle may be referred to as the insertion angle and the axis may be referred to as an insertion axis. And while in this example, a needle guide is not defined in the lower surface 122, in some examples, a needle guide may be defined in the lower surface 122 and correspond to the orientation of the needle guide 128 defined in the upper surface 120.

Figure 3:
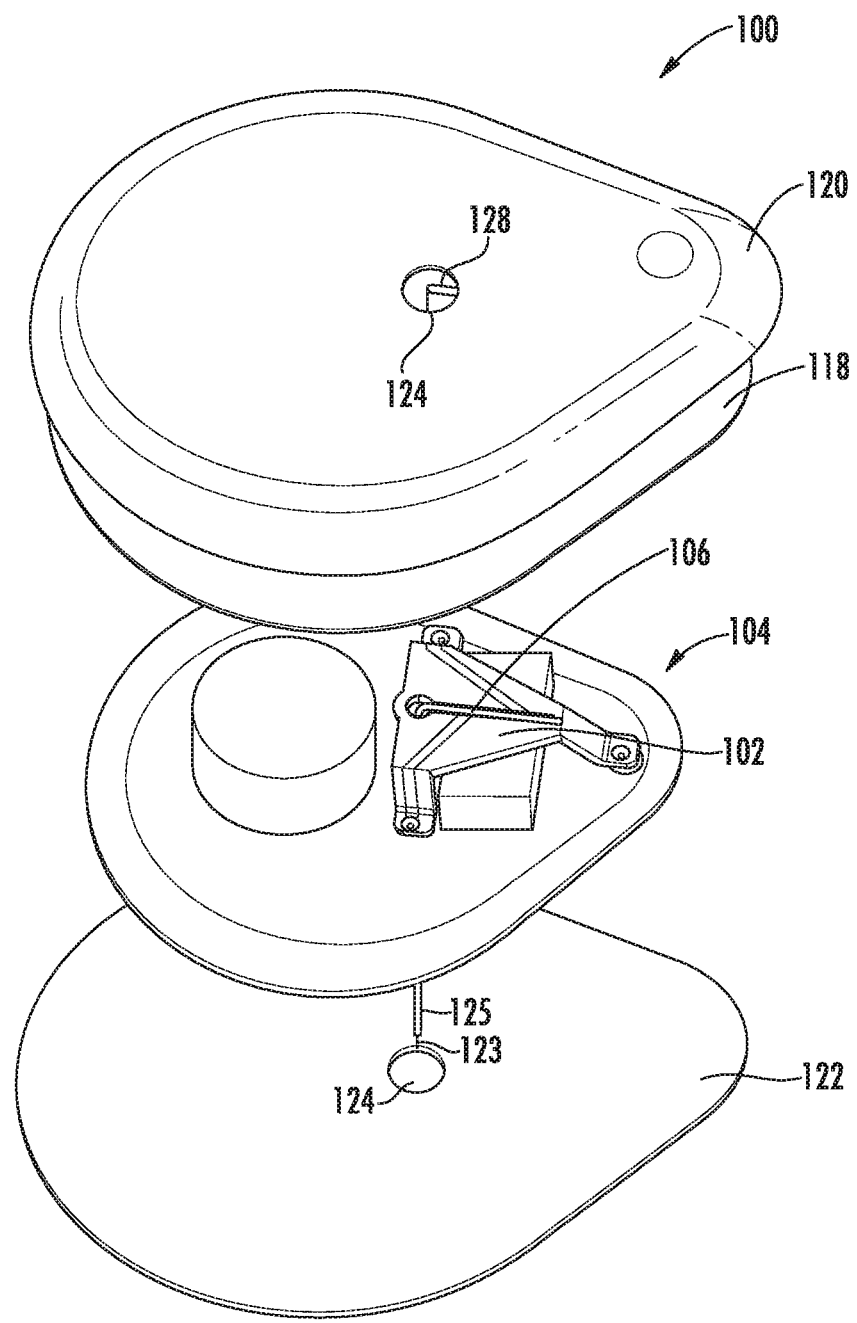
FIGS. 3-6 show example wearable biosensor having needle alignment features.

Referring now to FIG. 3, FIG. 3 shows the example housing 100 of FIG. 1 as well as sensor electronics 104 included between the upper and lower portions 120, 122 of the housing. As can be seen, the sensor electronics 104 include a sensor wire 106 that is physically coupled to a support structure 102. The support structure 102 in this example includes a tripod structure with an upper surface to physically couple and support the sensor wire 106 and to electrically couple the sensor wire 106 to electronics disposed within the housing. However any suitable support structure for the sensor wire may be employed. The sensor wire 106 extends along the upper surface of the support structure 102 and downward through a hole in a support structure 102 and through the hole 124 in the bottom portion 122 of the housing. The portion 125 of the sensor wire that extends below the lower portion 122 of the housing will be inserted into a wearer's skin to measure biometric information about the wearer, such as glucose level.

As discussed above, the upper and lower portions 120, 122 of the housing define holes 126, 124 to enable a needle to be inserted through the housing to assist with inserting the sensor wire 106 into the wearer's skin. In addition, the needle guide 128 is positioned to align with a portion of the sensor wire 106. The needle guide 128 thereby serves both to protect the sensor wire 106 from a needle striking the sensor wire 106 as it is being inserted, such as by striking the top of the needle, contacting or abrading the sensor wire 106 as the needle slides along the length of the sensor wire 106, or from rotating and striking the sensor wire 106, and also to help align the needle with the sensor wire 106.

To apply the biosensor 100, the wearer may extend a needle through the housing via the two holes 126, 124 such that the needle extends along the same axis 123 as the sensor wire 106, and extends further below the biosensor 100 than the sensor wire 106. For example, the sensor wire 106 may extend a few millimeters ("mm") to a centimeter ("cm") below the lower portion 122 of the biosensor 100, while the needle may extend another 1-5 mm farther than the sensor wire 106. After extending the needle through the housing, the wearer may then press the biosensor 100 and needle against her skin, thereby puncturing her skin with the needle and inserting the sensor wire 106 into the puncture wound. An adhesive applied the underside of the lower portion 122 of the biosensor 100 may then adhere the biosensor 100 to the wearer's skin. The wearer may then withdraw the needle, leaving the biosensor in place with the sensor wire 106 inserted into her skin.

Figure 4:
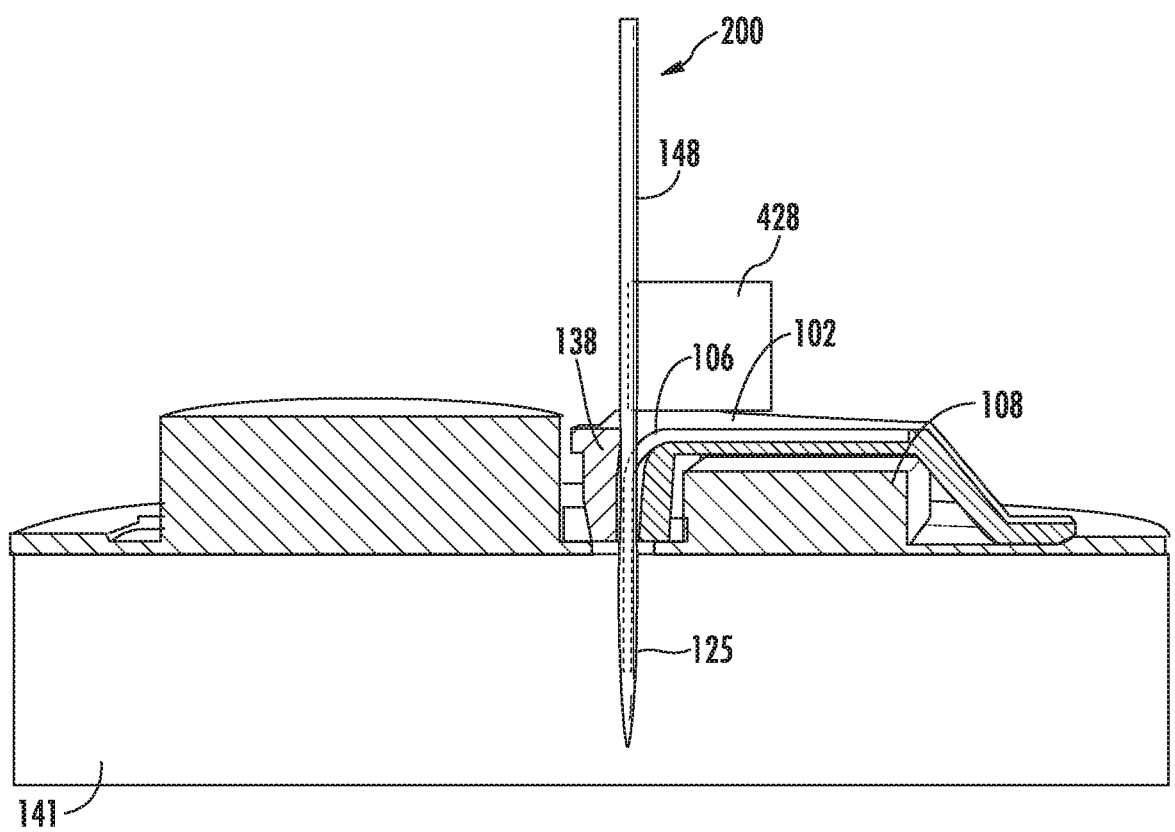

FIG. 4 shows a cross-section of the biosensor 100 to illustrate a needle 200 extending through the bottom of the biosensor 100 and into the wearer's skin 141 to assist with inserting the sensor wire 106 into the skin 141. As can be seen, the needle 200 extends downward through the biosensor to puncture the skin 141 while also aligning axially with the portion 125 of the sensor wire 106 that extends into the skin 141.

In addition, in this example, the biosensor 100 also includes a needle guide 428 physically coupled to the support structure 102 and engaged with the needle 148. In this example, the needle guide 428 is shown as a rectangular tab extending upward from the support structure 102. As can be seen, the needle guide 428 extends into and along a portion of the pathway traversed by the needle 200 and is oriented to align with a portion of the sensor wire 125. The needle guide 428 is thereby able to align the needle 200 with the sensor wire 106, and to prevent the needle 200 from contacting and potentially damaging the sensor wire 106. And while the needle guide 428 in this example is physically coupled to the support structure 102, it may be integrally formed as a part of the support structure, or may be one of multiple needle guides, which may be formed as a part of the holes 126, 124 shown in FIGS. 1-3 or otherwise positioned within the housing 100 and extending into the pathway to be traversed by the needle 200. For example, the needle guide 428 may be formed on a lower portion of the support structure or within the hole on the lower portion of the housing 100.

Figure 5:
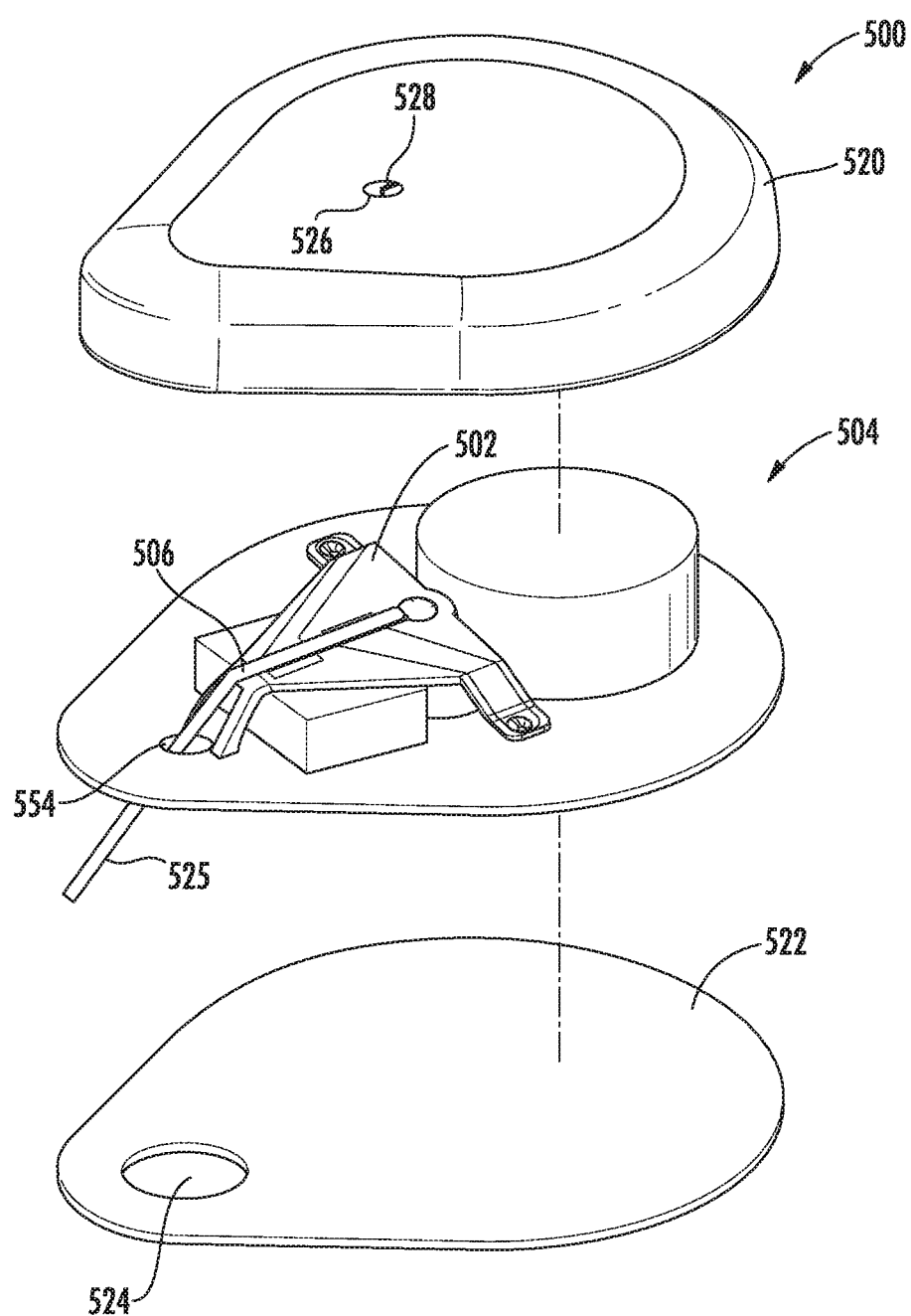

Referring now to FIG. 5, FIG. 5 shows another example biosensor 500 that includes a needle alignment feature to assist with applying the biosensor to a wearer. The example biosensor 500 includes upper and lower portions 520, 522 of a housing, each of which defines a hole 526, 524 to receive a needle. In this example, however, the two holes 526, 524 are aligned along an axis that is along an insertion angle of substantially 45 degrees, where in this example the hole 526 in the upper portion 520 is smaller than the hole 524 in the lower portion 522, e.g., it has one or more of a smaller diameter, smaller cross-sectional area, shorter perimeter, etc. Thus, the sensor wire 506 in this example does not extend perpendicularly through the hole 524 defined in the lower portion 504 of the biosensor 500. Instead, the sensor wire 506 is supported on a support structure 502 and has a bend of substantially 45 degrees near the edge of the support structure 502. The sensor wire 506 then extends through a hole 554 defined in the electronics portion 504 of the biosensor 500 and a portion 525 of the sensor wire extends through the hole 524 defined in the lower portion 522 of the housing.

Further, as can be seen, a needle guide 528 is defined in the upper portion 520 of the housing to engage with a needle having a cross-section corresponding to the shape of the hole 526 and the needle guide 528. However, in this example, the hole 526 and the needle guide 528 are defined to guide the needle at a 45 degree angle along an axis aligned with the portion 525 of the sensor wire that extends below the biosensor. And while the example shown in FIG. 5 employs a sensor wire 506 having an insertion angle of 45 degrees, other insertion angles may be used.

When a wearer uses such an example biosensor 500, she may engage a needle with the hole 526 and projection 528 in the upper portion 520 of the housing and insert the needle through the hole 526 along the insertion angle through the housing and through the hole 524 in the lower portion 522 of the housing. Insertion of the needle also engages the needle with the sensor wire 506 by aligning them along a common axis, though the needle in some examples may not contact the sensor wire. Further, the needle guide 528 may prevent the needle from being inserted at the wrong orientation, thereby potentially striking and damaging the sensor wire. It may further prevent the needle from rotating or otherwise contacting the sensor wire 506 and potentially damaging the sensor wire 506. After inserting the needle, the user may then press the needle/biosensor assembly against her skin to puncture it using the needle and to adhere the biosensor 500 to her skin. Because the sensor wire 506 and needle are aligned along a common axis, insertion of the needle also allows the portion 525 of the sensor wire 506 to follow the needle into the puncture. The wearer may then withdraw the needle from the biosensor 500, leaving the portion 525 of the sensor wire in place beneath the wearer's skin.

Figure 6:
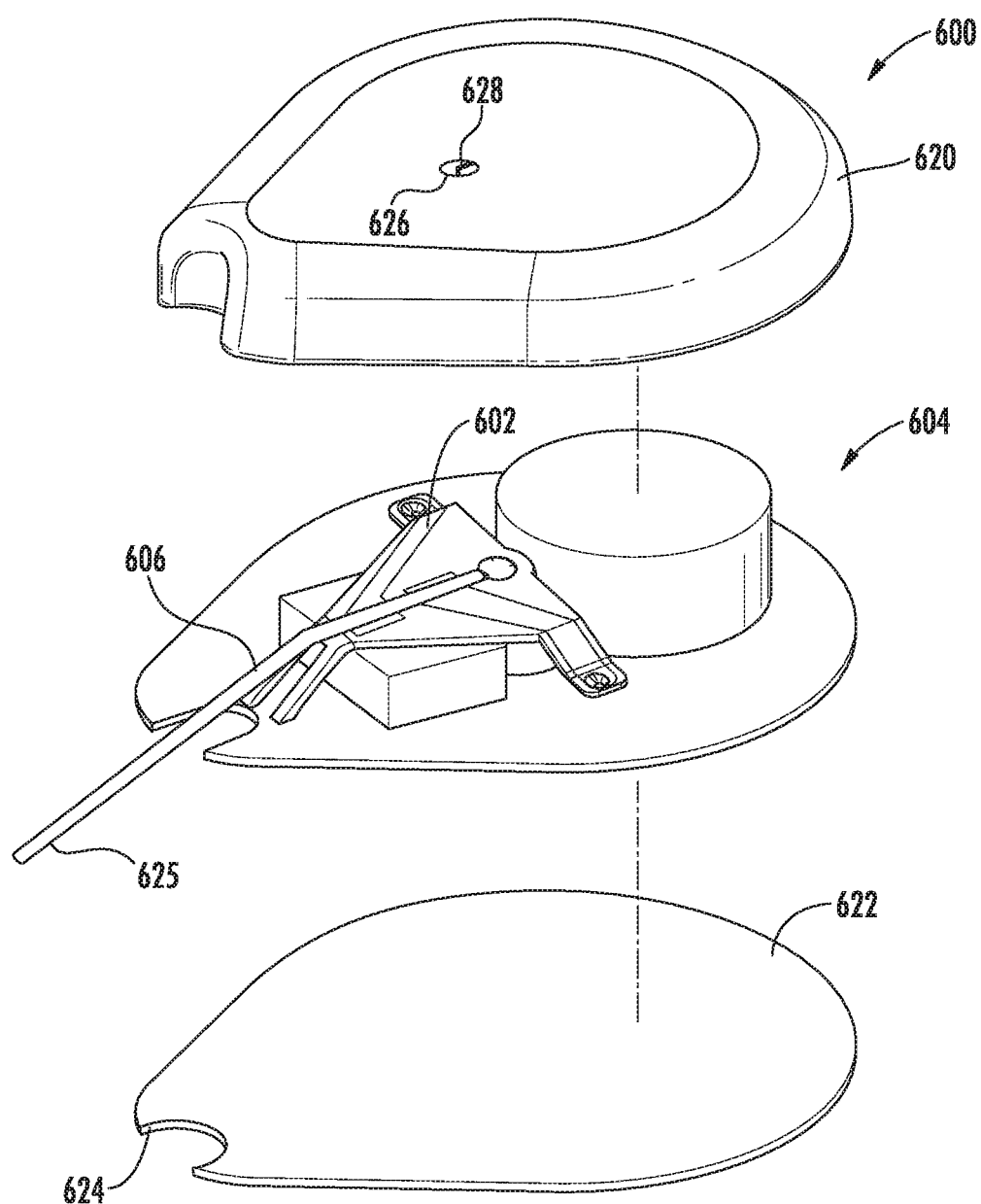

Referring now to FIG. 6, FIG. 6 shows an example biosensor 600 that includes a needle alignment feature to assist with applying the biosensor to a wearer. The example biosensor 600 includes upper and lower portions 620, 622 of a housing, each of which defines a hole 626, 624. As with the example biosensor shown in FIG. 5, the two holes are aligned along an axis having a non-zero insertion angle, such as the oblique angle illustrated in this example. Instead, in this example, the insertion angle is substantially 60 degrees. Thus, the sensor wire 606, which is supported by support structure 602, extends horizontally along the support structure and bends downward at substantially a 30 degree angle from the horizontal. A portion 625 of the sensor wire 606 extends downward through the hole 624 defined in the lower portion 622 of the housing. The needle guide 628 is again positioned to extending into and across a portion of the pathway the needle will traverse between the holes 626, 624 in the upper and lower portions 620, 633 of the housing. In addition, as discussed above with respect to FIGS. 1-5, the needle guide is oriented to align with the sensor wire 606 to prevent a needle from contacting and potentially damaging the sensor wire 606.

Figure 7:
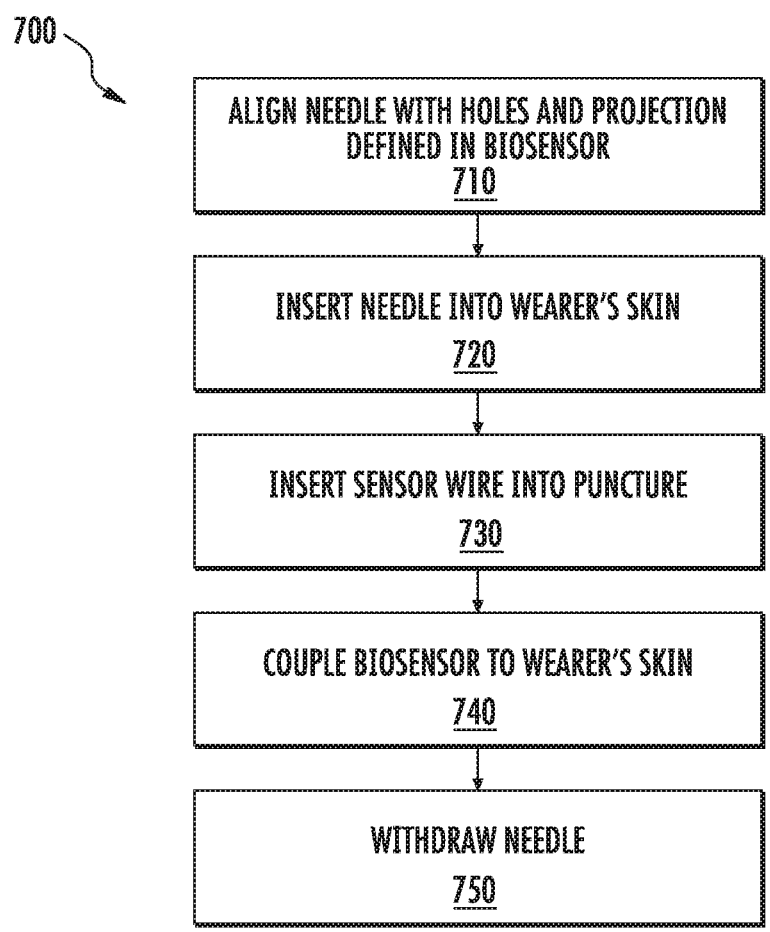
FIGS. 7-8 show example methods for needle alignment for wearable biosensors.

Referring now to FIG. 7, FIG. 7 shows an example method 700 for needle alignment for wearable biosensors. The method 700 will be described with respect to the example biosensor 300 shown in FIG. 3, but may be used with any suitable biosensor according to this disclosure.

At block 710, a wearer aligns a needle with a hole 124 and a projection 128 defined in an upper portion 122 of a housing of a wearable medical device 100. In this example, the wearer uses a needle having a C-shaped cross-section, such as the needle 200 shown in FIGS. 2A-2C. After aligning the needle with the hole 124 and projection 128, the wearer inserts the needle through the biosensor along an insertion angle. In this example, the insertion angle is substantially 0 degrees; however, in other examples, the insertion angle may be any suitable insertion angle, such as between 0 and 60 degrees.

At block 720, the wearer inserts the needle into her skin at an insertion point to create a puncture.

At block 730, the wearer inserts a portion 125 of the sensor wire 106 into her skin through the puncture.

At block 740, the wearer physically couples the biosensor 100 to her skin. In this example, the exterior of the lower portion 122 of the housing has a pressure-sensitive adhesive layer deposited on it. Thus, the wearer presses the biosensor 100 against her skin to adhere it in place. In other examples, the wearer may first apply an adhesive material to her skin or the housing, or may use an adhesive tape to physically couple the biosensor 100 to her skin.

At block 750, the wearer withdraws the needle from the wearer's skin and from the biosensor 100, leaving the biosensor 100 in place on the wearer's skin.

Figure 8:
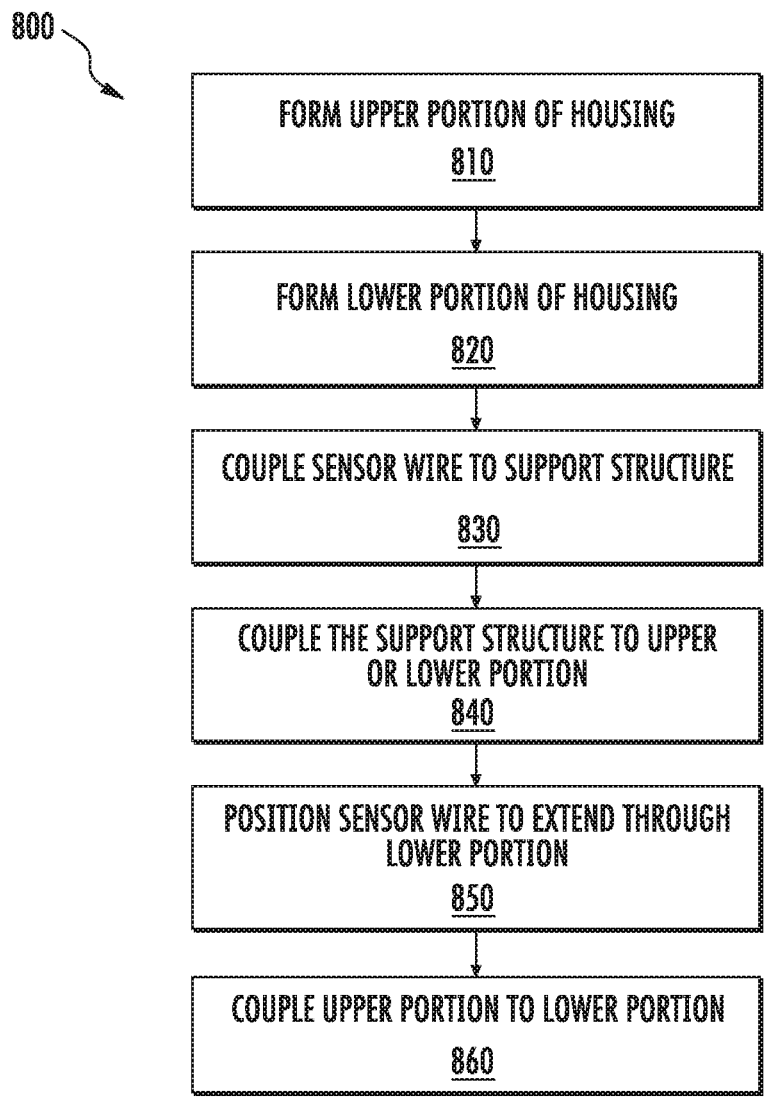

Referring now to FIG. 8, FIG. 8 shows an example method 800 of manufacturing a wearable biosensor having a needle alignment feature. The method 800 will be described with respect to the example biosensor 300 shown in FIG. 3, but may be used with any suitable biosensor according to this disclosure.

At block 810, a manufacturer forms an upper portion 120 of a housing, the upper portion 120 defining a first opening 126 extending through the upper portion, the first opening 126 having a perimeter, the upper portion 120 further defining a projection 128 extending from the perimeter of the opening 126 and across a portion of the opening. In this example, the upper portion 120 is formed by injection molding, but in other examples, the upper portion may be formed by casting or other suitable methods. In this example, the projection 128 extends from the perimeter to a centerline of an insertion axis corresponding to an insertion angle.

At block 820, the manufacturer forms a lower portion 122 of the housing, the lower portion 122 defining a second opening 124 extending through the lower portion 122. As discussed above with respect to the upper portion 120, the lower portion 122 may be formed by injection molding, casting, or any other suitable method.

At block 830, the manufacturer physically couples a sensor wire to a support structure. In this example, the sensor wire 106 is physically coupled to a support structure 102 mounted to a printed circuit board ("PCB") of an electronics layer 104. However, in some examples, the sensor wire may be directly physically coupled to the PCB or to another electronic component, which then serves as the support structure. In addition, the sensor wire may be electrically coupled to one or more electrical contacts formed on the support structure or another structure, such as a PCB or other electrical component. In this example, the sensor wire 106 was manufactured with a bend in it to correspond to the desired insertion angle and along the insertion axis for the biosensor. However, in some examples, the method 800 may further comprise a step of bending the sensor wire 106 to a desired insertion angle after the sensor wire 106 is physically coupled to the support structure.

At block 840, the manufacturer physically couples the support structure to at least one of the upper portion or the lower portion such that the support structure 102 is disposed within the cavity. In this example, the support structure 102 is attached to an electronics layer 104 that is physically coupled to the interior of the lower portion 122 of the housing; however, in other examples, the support structure 102 may be instead physically coupled directly to the lower portion 122 or the upper portion 120 of the housing.

At block 850, the manufacturer physically couples the upper portion to the lower portion to define a cavity between the upper portion and the lower portion, the cavity extending from the first opening to the second opening and establishing a substantially unobstructed pathway from the first opening to the second opening. In this example, the physical coupling seals the electronics layer 104 within the housing and causes a portion 125 of the sensor wire 106 to extend through the second hole 124.

While the foregoing methods 700, 800 have been described in a particular order, the ordering of steps can vary according to different examples. For example, blocks 810-

850 can occur in any order. In addition, the methods 700, 800 can include additional steps, or may not include each of the described steps. Rather, these methods 700, 800 are provided merely as examples according to the present disclosure.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. An invasive sensor device comprising:
   an insertion needle having a channel spanning at least a portion of a length of the insertion needle;
   a housing comprising an upper portion and a lower portion, the housing defining a cavity between the upper portion and the lower portion and the housing being configured to be worn on a wearer's skin, wherein:
   the upper portion defines a first opening extending through the upper portion to the cavity,
   the lower portion defines a second opening extending through the lower portion to the cavity, and
   the first opening and the second opening are part of a pathway to enable the insertion needle to be inserted through the housing; and
   a needle guide including a projection extending into and along a portion of the pathway and aligned with a sensor wire to align the insertion needle with the sensor wire and protect the sensor wire from being contacted by the insertion needle when the insertion needle is within the pathway, the projection being received by the channel of the insertion needle as the insertion needle is inserted through the housing.

2. The device of claim 1, wherein the projection extends from a portion of a perimeter of at least one of the first or second opening.

3. The device of claim 1, wherein the upper portion and the lower portion are discrete pieces, and wherein the upper portion is physically coupled to the lower portion to form at least a portion of the housing.

4. The device of claim 1, wherein the first and second openings have different sizes within parallel cross-sectional planes or different cross-sectional shapes within parallel cross-sectional planes.

5. The device of claim 1, further comprising:
   a support structure disposed within the cavity and physically coupled to at least one of the upper portion or the lower portion;
   the sensor wire physically coupled to the support structure and extending from the support structure into the pathway and through the second opening; and
   wherein:
   the cavity extends along an axis from the first opening to the second opening, and
   the sensor wire is arranged to extend through the second opening parallel to or coaxially with the axis.

6. The device of claim 5, wherein the needle guide is physically coupled to the support structure.

7. The device of claim 5, wherein the support structure further comprises the needle guide.

8. The device of claim 5, wherein the axis is perpendicular to a lower surface of the lower portion of the housing.

9. The device of claim 5, wherein the axis is at an oblique angle to a lower surface of the lower portion of the housing.

10. The device of claim 1, wherein the first and second openings each define cross-sections to receive the insertion needle, and the cavity is sized to allow the insertion needle to traverse the cavity from the first opening through the second opening, the insertion needle having a cross-section corresponding to a perimeter of the first opening and to engage with the needle guide.

11. The device of claim 1, wherein at least one of the first or second openings has a circular, polygonal, or hemispherical cross-section.

12. An invasive sensor device comprising:
    an insertion needle having a channel spanning at least a portion of a length of the insertion needle;
    a housing comprising an upper portion and a lower portion, the housing defining a cavity between the upper portion and the lower portion and the housing being configured to be worn on a wearer's skin, wherein:
    the upper portion defines a first opening extending through the upper portion to the cavity,
    the lower portion defines a second opening extending through the lower portion to the cavity, and
    the first opening and the second opening are part of a pathway to enable the insertion needle to be inserted through the housing; and
    a needle guide including a projection extending into and along a portion of the pathway and aligned with a sensor wire to align the insertion needle with the sensor wire, the projection establishing a shape within the pathway corresponding to the channel of the insertion needle.

13. The device of claim 12, wherein the projection extends from a portion of a perimeter of at least one of the first or second opening.

14. The device of claim 12, wherein the upper portion and the lower portion are discrete pieces, and wherein the upper portion is physically coupled to the lower portion to form at least a portion of the housing.

15. The device of claim 12, wherein the first and second openings have different sizes within parallel cross-sectional planes or different cross-sectional shapes within parallel cross-sectional planes.

16. The device of claim 12, further comprising:
    a support structure disposed within the cavity and physically coupled to at least one of the upper portion or the lower portion;

the sensor wire physically coupled to the support structure and extending from the support structure into the pathway and through the second opening; and wherein:

the cavity extends along an axis from the first opening to the second opening, and the sensor wire is arranged to extend through the second opening parallel to or coaxially with the axis.

17. The device of claim 16, wherein the needle guide is physically coupled to the support structure.

18. The device of claim 16, wherein the support structure further comprises the needle guide.

19. The device of claim 16, wherein the axis is perpendicular to a lower surface of the lower portion of the housing.

20. The device of claim 16, wherein the axis is at an oblique angle to a lower surface of the lower portion of the housing.

* * * * *